United States Patent
Scofield et al.

(10) Patent No.: US 9,506,081 B1
(45) Date of Patent: Nov. 29, 2016

(54) **TRANSGENE CONSTRUCT TO IMPROVE *FUSARIUM* HEAD BLIGHT RESISTANCE IN WHEAT AND BARLEY**

(71) Applicants: The United States of America, as represented by the Secretary of Agriculture, Washington, DC (US); Kansas State University Research Foundation, Manhattan, KS (US); Purdue Research Foundation, West Lafayette, IN (US)

(72) Inventors: Steven R. Scofield, West Lafayette, IN (US); Megan E. Gillespie, St. Louis, MO (US); Amanda S. Brandt, Battle Ground, IN (US); Harold N. Trick, Olsburg, KS (US); Lynn S. Dahleen, Fargo, ND (US)

(73) Assignees: The United States of America, as represented by the Secretary of Agriculture, Washington, DC (US); Kansas State University Research Foundation, Manhanttan, KS (US); Purdue Research Foundation, West Lafayetta, IN (US)

( * ) Notice: Subject to any disclaimer, the term of this patent is extended or adjusted under 35 U.S.C. 154(b) by 275 days.

(21) Appl. No.: 14/163,248

(22) Filed: Jan. 24, 2014

Related U.S. Application Data

(60) Provisional application No. 61/758,857, filed on Jan. 31, 2013.

(51) Int. Cl.
  *C12N 15/82* (2006.01)
(52) U.S. Cl.
  CPC .................. *C12N 15/8282* (2013.01)
(58) Field of Classification Search
  None
  See application file for complete search history.

(56) References Cited

U.S. PATENT DOCUMENTS

| | | | |
|---|---|---|---|
| 6,664,446 B2 | 12/2003 | Heard et al. | |
| 2012/0137382 A1* | 5/2012 | Repetti | C07K 14/415 800/263 |

FOREIGN PATENT DOCUMENTS

| | | | | |
|---|---|---|---|---|
| WO | WO 2010039750 A2 * | 4/2010 | ......... | C12N 15/8261 |

OTHER PUBLICATIONS

Badawi (Functional Genomics of the AP2 Transcription Factor Family in Cereals. PhD Thesis. Apr. 2008).*
Gottwald et al (Jasmonate and ethylene dependent defence gene expression and suppression of fungal virulence factors: two essential mechanisms of *Fusarium* head blight resistance in wheat? BMC Genomics. 13:369, p. 1-22, 2012).*
Tai, Yin-Shan, et al., "The Potential Wheat Signaling Pathways in Response to Abiotic Stress", American Journal of Plant Physiology, 2 (5), 2007, pp. 295-302.

* cited by examiner

*Primary Examiner* — Medina A Ibrahim
*Assistant Examiner* — Wayne Zhong
(74) *Attorney, Agent, or Firm* — John D. Fado; David L. Marks

(57) ABSTRACT

Resistance of plants, particularly wheat and barley, to *Fusarium* head blight (FHB) and other *Fusarium*-related diseases may be induced or enhanced by transformation with a nucleic acid (DNA) construct comprising a nucleic acid sequence encoding the wheat ethylene-responsive transcription factor TaERF7-1 operatively linked to a promoter effective for expression in the plant. Plants transformed with the construct exhibit increased resistance to FHB and other *Fusarium*-related diseases in comparison to a non-transformed control plant. The transgenic plants may be produced from any plant, tissue or cell which is capable of regeneration, by transformation with the construct. Transformed plants, plant tissue or plant cells comprising the construct are selected, and the transgenic plant is generated therefrom.

15 Claims, 2 Drawing Sheets

```
GGATCCTTGATCCGGCCTCGCGATGTGCGGCGGAGCCATCCTCGCGGGCTTCAT
CCCGCCGTCGGCGGCCGCCGCGGCGGCCAAGGCGGCGGCAGCCAAGAAGAAGC
AGCAGCAGCGCAGCGTGACGGCCGACTCGCTGTGGCCGGGCCTGCGGAAAAAG
GCGGCCGAGGAGGAGGACTTCGAGGCCGACTTCCGCGACTTCGAGCGGGACTCC
AGCGACGACGACGCCGTGGTCGAGGAGGTTCCACCGCCGCCGGCCTCGGCGGG
TTTCGCCTTCGCCGCCGCGGCCGAGGTCGCGCCCCGGCCCCTGCCCGCCTAGA
TGCTGTTCAACATGATGGACCTGCTGCCAAACAAGTAAAGCGCGTTCGGAAGAATC
AGTACAGAGGCATCCGCCAGCGTCCCTGGGGGAAATGGGCAGCTGAAATCCGTG
ACCCTAGCAAGGGTGTCCGGGTTTGGCTCGGGACATACGACACTGCTGAGGAGG
CAGCAAGGGCATATGATGCTGAAGCCCGCAAGATTCGTGGCAAGAAGGCCAAGGT
CAATTTTCCTGAGGATGCTCCAACTGTTCAGAAGTCTACTCTGAAGCCAACTGCCG
CTAAATCAGCAAAGCTGGCTCCACCTCCGAAGGCCTGCGAGGATGAGCCTTTCAA
TCATCTGAGCAGAGGAGACAATGATTTGTTCGCGATGTTCGCCTTCAATGACAAGA
AAGTTCCTGCGAAGCCAGCTGAAAGTGTGGATTCCCTTCTTCCGGTGAAACCTCTT
GTGCCCACTGAGACATTCGGGATGAACATGCTCTCTGACCAGAGTAGCAACTCATT
TGGCTCTACTGACTTTGGGTGGGACGATGAGGTCATGACCCCGGACTACACGTCC
GTCTTCGTCCCGAATGCTGCTGCCATGCCGGCATACGGCGAGCCCGCTTACCTGC
AAGGTGGAGCTCCAAAGAGAATGAGGAACAACTTTGGCGTGGCCGTGCTGCCTCA
GGGAAATGTTGCACAAGACATCCCTGCTTTTGACCATGAGATGAAGTACTCGTTGC
CTTATGTTGAGAGCAGCTCGGACGGATCAATGGACAGCCTTCTGCTGAATGGTGC
GATGCAGGACGGGGCAAGCAGTGGGGATCTCTGGAGCCTCGATGAGCTCTTCAT
GGCGGCTGGTGGTTACTGAGGGTTCTTGTCTGTGTGGATCC
```

Figure 2

SEQUENCE LISTING

```
<160> NUMBER OF SEQ ID NOS: 2

<210> SEQ ID NO 1
<211> LENGTH: 381
<212> TYPE: PRT
<213> ORGANISM: Triticum aestivum

<400> SEQUENCE: 1

Met Cys Gly Gly Ala Ile Leu Ala Gly Phe Ile Pro Pro Ser Ala Ala
1               5                   10                  15

Ala Ala Ala Ala Lys Ala Ala Ala Ala Lys Lys Lys Gln Gln Gln Arg
            20                  25                  30

Ser Val Thr Ala Asp Ser Leu Trp Pro Gly Leu Arg Lys Lys Ala Ala
        35                  40                  45
```

```
Glu Glu Glu Asp Phe Glu Ala Asp Phe Arg Asp Phe Glu Arg Asp Ser
    50                  55                  60

Ser Asp Asp Asp Ala Val Val Glu Glu Val Pro Pro Pro Ala Ser
65                  70                  75                  80

Ala Gly Phe Ala Phe Ala Ala Ala Glu Val Ala Pro Pro Ala Pro
                85                  90                  95

Ala Arg Leu Asp Ala Val Gln His Asp Gly Pro Ala Ala Lys Gln Val
                100                 105                 110

Lys Arg Val Arg Lys Asn Gln Tyr Arg Gly Ile Arg Gln Arg Pro Trp
                115                 120                 125

Gly Lys Trp Ala Ala Glu Ile Arg Asp Pro Ser Lys Gly Val Arg Val
130                 135                 140

Trp Leu Gly Thr Tyr Asp Thr Ala Glu Glu Ala Ala Arg Ala Tyr Asp
145                 150                 155                 160

Ala Glu Ala Arg Lys Ile Arg Gly Lys Lys Ala Lys Val Asn Phe Pro
                165                 170                 175

Glu Asp Ala Pro Thr Val Gln Lys Ser Thr Leu Lys Pro Thr Ala Ala
                180                 185                 190

Lys Ser Ala Lys Leu Ala Pro Pro Lys Ala Cys Glu Asp Glu Pro
    195                 200                 205

Phe Asn His Leu Ser Arg Gly Asp Asn Asp Leu Phe Ala Met Phe Ala
    210                 215                 220

Phe Asn Asp Lys Lys Val Pro Ala Lys Pro Ala Glu Ser Val Asp Ser
225                 230                 235                 240

Leu Leu Pro Val Lys Pro Leu Val Pro Thr Glu Thr Phe Gly Met Asn
                245                 250                 255

Met Leu Ser Asp Gln Ser Ser Asn Ser Phe Gly Ser Thr Asp Phe Gly
                260                 265                 270

Trp Asp Asp Glu Val Met Thr Pro Asp Tyr Thr Ser Val Phe Val Pro
                275                 280                 285

Asn Ala Ala Ala Met Pro Ala Tyr Gly Glu Pro Ala Tyr Leu Gln Gly
                290                 295                 300

Gly Ala Pro Lys Arg Met Arg Asn Asn Phe Gly Val Ala Val Leu Pro
305                 310                 315                 320

Gln Gly Asn Val Ala Gln Asp Ile Pro Ala Phe Asp His Glu Met Lys
                325                 330                 335

Tyr Ser Leu Pro Tyr Val Glu Ser Ser Asp Gly Ser Met Asp Ser
                340                 345                 350

Leu Leu Leu Asn Gly Ala Met Gln Asp Gly Ala Ser Ser Gly Asp Leu
                355                 360                 365

Trp Ser Leu Asp Glu Leu Phe Met Ala Ala Gly Gly Tyr
370                 375                 380
```

<210> SEQ ID NO 2
<211> LENGTH: 1190
<212> TYPE: DNA
<213> ORGANISM: Triticum aestivum

<400> SEQUENCE: 2

```
ggatccttga tccggcctcg cgatgtgcgg cggagccatc ctcgcgggct tcatcccgcc    60
gtcggcggcc gccgcggcgg ccaaggcggc ggcagccaag aagaagcagc agcagcgcag   120
cgtgacggcc gactcgctgt ggccgggcct gcggaaaaag gcggccgagg aggaggactt   180
cgaggccgac ttccgcgact tcgagcggga ctccagcgac gacgacgccg tggtcgagga   240
```

```
ggttccaccg ccgccggcct cggcgggttt cgccttcgcc gccgcggccg aggtcgcgcc       300
cccggcccct gcccgcctag atgctgttca acatgatgga cctgctgcca aacaagtaaa       360
gcgcgttcgg aagaatcagt acagaggcat ccgccagcgt ccctggggga aatgggcagc       420
tgaaatccgt gaccctagca agggtgtccg ggtttggctc gggacatacg acactgctga       480
ggaggcagca agggcatatg atgctgaagc ccgcaagatt cgtggcaaga aggccaaggt       540
caattttcct gaggatgctc caactgttca gaagtctact ctgaagccaa ctgccgctaa       600
atcagcaaag ctggctccac ctccgaaggc ctgcgaggat gagcctttca atcatctgag       660
cagaggagac aatgatttgt tcgcgatgtt cgccttcaat gacaagaaag ttcctgcgaa       720
gccagctgaa agtgtggatt cccttcttcc ggtgaaacct cttgtgccca ctgagacatt       780
cgggatgaac atgctctctg accagagtag caactcattt ggctctactg actttgggtg       840
ggacgatgag gtcatgaccc cggactacac gtccgtcttc gtcccgaatg ctgctgccat       900
gccggcatac ggcgagcccg cttacctgca aggtggagct ccaaagagaa tgaggaacaa       960
cttcggcgtg gccgtgctgc ctcagggaaa tgttgcacaa gacatccctg cttttgacca      1020
tgagatgaag tactcgttgc cttatgttga gagcagctcg gacggatcaa tggacagcct      1080
tctgctgaat ggtgcgatgc aggacggggc aagcagtggg gatctctgga gcctcgatga      1140
gctcttcatg gcggctggtg gttactgagg gttcttgtct gtgtggatcc                 1190
```

TRANSGENE CONSTRUCT TO IMPROVE FUSARIUM HEAD BLIGHT RESISTANCE IN WHEAT AND BARLEY

CROSS-REFERENCE TO RELATED APPLICATION

This present application claims priority under 35 U.S.C. §119(e) to U.S. Provisional Ser. No. 61/758,857, which was filed on Jan. 31, 2013, and is hereby incorporated by reference.

BACKGROUND OF THE INVENTION

1. Field of the Invention

This invention is drawn to transgenic plants with improved resistance to *Fusarium* head blight and nucleic acid constructs used in their production.

2. Description of the Prior Art

Wheat (*Triticum aestivum*) is fundamental to the world's food supply. Worldwide, one of the most serious threats to wheat production is *Fusarium* head blight (FHB) (Windels. 2000. Economic and social impacts of *Fusarium* head blight: changing farms and rural communities in the northern great plains. Phytopathology. 90:17-21; Dean et al. 2012. The Top 10 fungal pathogens in molecular plant pathology. Mol Plant Pathol. 13:414-430), which is caused when *Fusarium graminearum* (Schwabe) (teleomorph: *Gibberella zeae*) infects the spike. FHB, also called "scab", results in significant yield loss and grain contaminated with the mycotoxin deoxynivalenol (DON). Losses for the United States wheat and barley harvests from 1998 to 2000 have been estimated to total $2.7 billion dollars (Wood et al. 1999. Fighting *Fusarium*. In Agricultural Research. United States Department of Agriculture, Agricultural Research Service, Beltsville, Md.). Aside from yield reduction, contamination of grain with DON is a serious health problem as it can cause illness in both humans and animals. The US Food and Drug Administration has advised that DON concentration in products not exceed 1 ppm for humans and 5 ppm for livestock (Van Egmond and Dekker. 1995. Worldwide regulations for mycotoxins in 1994. Natural Toxins. 3:332-336). Grain presented at storage elevators is tested for DON content, and producers are assessed price penalties for higher levels of contamination. Unfortunately FHB is becoming more frequent; in large part because the *F. graminearum* is able to grow saprophytically on the debris of corn. As corn acreage is expanding rapidly and the adoption of conservation tillage is increasing, wheat is frequently planted into soil with an ample source of FHB inoculum (Bai and Shaner. 2004. Management and resistance in wheat and barley to *Fusarium* head blight. Annual Review of Phytopathology. 42:135-161).

FHB can occur anywhere in the world where rainfall or high humidity occurs during flowering (Steffenson. 2003. *Fusarium* head blight of barley: impact, epidemics and strategies for identifying and utilizing genetic resistance. In L K J, B W R, eds, *Fusarium* Head Blight of Wheat and Barley. APS Press, St. Paul, Minn., pp 241-295; Bai and Shaner. 2004. ibid.). Airborne *F. graminearum* spores are thought to enter the spikelet through openings in the palea and lemma tissue. Once it has entered the spikelet the fungus initially grows without killing cells, although it is debated whether this represents a true biotrophic phase as intracellular growth has not been observed during this initial phase of infection (Bushnell et al. 2003. Histology and physiology of *Fusarium* head blight. In K Leonard, W R Bushnell, eds, *Fusarium* head blight of wheat and barley. APS Press, St. Paul, Minn., pp 44-83; Jansen et al. 2005. Infection patterns in barley and wheat spikes inoculated with wild-type and trichodiene synthase gene disrupted *Fusarium graminearum*. Proceedings of the National Academy of Sciences of the United States of America. 102:16892-16897; Trail. 2009. For blighted waves of grain: *Fusarium graminearum* in the postgenomics era. Plant physiology. 149:103-110; Brown et al. 2010. The infection biology of *Fusarium graminearum*: defining the pathways of spikelet to spikelet colonisation in wheat ears. Fungal Biol. 114:555-571). However, within hours the pathogen transitions to a clearly necrotrophic phase accompanied by rapid growth, intracellular invasion and the biosynthesis of DON, which is essential for spreading through the rachis and into neighboring spikelets (Bai et al. 2001. Deoxynivalenol-nonproducing *Fusarium graminearum* causes initial infection, but does not cause disease spread in wheat spikes. Mycopathologia. 153:91-98; Jansen et al. 2005. ibid).

Intense efforts have been made by wheat breeders to develop FHB resistant varieties, but none of these have strong resistance, as all identified sources of genetic resistance are Quantitative Trait Loci (QTL) that provide only partial protection (Mesterhazy. 2003. Breeding wheat for *Fusarium* head blight resistance in Europe. In K Leonard, W R Bushnell, eds, *Fusarium* head blight of wheat and barley. APS Press, St. Paul, Minn., pp 211-240; Bai and Shaner. 2004. ibid). In wheat the most widely utilized QTL is FHB1, located on chromosome 3BS (Anderson et al. 2008. Toward positional cloning of Fhb1, a major QTL for *Fusarium* head blight resistance in wheat. Cereal Research Communications. 36:195-201). Plants containing the FHB1 allele have what is defined as type II resistance or resistance to spread of infection, but not to initial infection (Schroeder and Christensen. 1963. Factors affecting resistance of wheat to scab caused by *Giberella zeae*. Phytopathology. 53:831-838). This type of resistance is assayed by point inoculating one spikelet and then observing whether infection spreads through the rachis and into neighboring spikelets.

Despite clear contribution of these loci to FHB resistance, little is known about the genes residing at the QTL or about the mechanisms of resistance. One of the reasons this research has been so difficult in wheat is the complexity of performing genetic analysis in an allohexaploid species. Given the difficulty of genetic analysis several groups have begun to study the FHB resistance response by characterizing the transcriptional changes that occur in resistant and susceptible interactions (Boddu et al. 2006. Transcriptome analysis of the barley-*Fusarium graminearum* interaction. Mol Plant Microbe Interact. 19:407-417; Bernardo et al. 2007. *Fusarium graminearum*-induced changes in gene expression between *Fusarium* head blight resistant and susceptible wheat cultivars. Funct Integr Genomics. 7:69-77; Boddu et al. 2007. Transcriptome analysis of trichothecenes-induced gene expression in barley. Mol Plant Microbe Interact. 20:1364-1375; Golkari et al. 2007. Microarray analysis of *Fusarium graminearum*-induced wheat gene: identification of organ-specific and differentially expressed genes. Plant Biotechnology Journal. 5:38-49; Kong et al. 2007. Expression analysis of defense-related genes in wheat in response to infection by *Fusarium graminearum*. Genome. 50:1038-1048; Desmond et al. 2008. Gene expression analysis of the wheat response to infection by *Fusarium pseudograminearum*. Physiological and Molecular Plant Pathology. 73:40-47; Li and Yen. 2008. Jasmonate and ethylene signaling pathway may mediate *Fusarium* head blight resistance in wheat. Crop Science.

48:1888-1895; Jia et al. 2009. Transcriptome analysis of a wheat near-isogenic line carrying *Fusarium* head blight-resistant and -susceptible alleles. MPMI. 1366-1378; Steiner et al. 2009. Differential gene expression of related wheat lines with contrasting levels of head blight resistance after *Fusarium graminearum* inoculation. Theor Appl Genet. 118:753-764; Ding et al. 2011. Resistance to hemi-biotrophic *F. graminearum* infection is associated with coordinated expression of diverse defense signaling pathways. PLoS One. 6:e19008; Walter and Doohan. 2011. Transcript profiling of the phytotoxic response of wheat to the *Fusarium* mycotoxin deoxynivalenol. Mycotoxin Research. 1-10). This analysis has pointed toward a key role for induction of the basal defense pathway, also known as PAMP-triggered immunity (PTI). PTI is one of the two main branches of active plant immune responses. It is triggered by the perception of a range of conserved pathogen-associated molecular patterns by the host's PAMP perception recognition receptors (PRRs).

Several studies examining gene expression changes during FHB have detected induction of the ethylene (ET)- and jasmonic acid (JA)-signaling pathways as key responses of wheat as it is challenged by *F. graminearum* (Li and Yen, 2008. ibid; Ding et al., 2011. ibid). The ET- and JA-signaling pathways are integral components of the basal defense response and are known to synergistically activate basal defense against a wide range of necrotrophic pathogens (Glazebrook. 2005. Contrasting mechanisms of defense against biotrophic and necrotrophic pathogens. Annual Review of Phytopathology. 43:205-227; Mengiste. 2012. Plant Immunity to Necrotrophs. Annu Rev Phytopathol.). ET-mediated responses, the subject of this report, are made up of ET-biosynthesis, perception, and signaling. ET-biosynthesis is up-regulated rapidly after many pathogens initiate infection. Perception of this gaseous hormone by ET-receptors results in the induction of a diverse array of ET-responsive transcription factors (ERFs), some of which have defense-specific functions. Defense components induced by ERFs include the PRR, FLS2 and BIK1, a receptor-kinase that supports the function of several PRRs, including FLS2, EFR and CERK1. Additional cellular and physiological changes associated with ET-signaling include induction of lignin synthesis (Mengiste. 2012. ibid) and formation of abscission zones. The study of Ding et al. (2011. ibid), which examined transcriptional and proteomic changes occurring at the very early stages of susceptible and resistant FHB interactions identified a possibly critical role for ET-signaling. Their analysis found a biphasic pattern of defense pathway expression. Within the first three hours of infection of susceptible and resistant genotypes, which likely corresponds to the biotrophic or asymptomatic phase of *F. graminearum* infection, elements of salicylic acid-mediated defense are induced. The second phase was defined as beginning at 12 hours after infection when genes associated with jasmonic acid-mediated defense are induced. However, it was observed that unique to the resistant genotype, genes involved in ET-biosynthesis and signaling are induced as early as 3-6 hours after infection. Ding et al suggested that activation of ET-signaling prior to JA-mediated defense in the resistant genotype is necessary for the JA-mediated defenses to have full activity.

However, Chen et al. (2009. *Fusarium graminearum* exploits ethylene signaling to colonize dicotyledonous and monocotyledonous plants. New Phytol. 182:975-983) proposed a very different role for ET-signaling in the FHB interaction. These authors developed an *Arabidopsis*-based model pathosystem for FHB in which *F. graminearum* infects detached leaves. Analysis of the behavior of *Arabidopsis* ET-signaling mutants in this pathosystem suggested that mutations eliminating ET-signaling conferred increased resistance to *F. graminearum*. They then conducted experiments in wheat that led them to conclude that *F. graminearum* exploits ET-signaling to create susceptibility to FHB.

Despite these and other advances, the need remains for plants with improved resistance to FHB.

SUMMARY OF THE INVENTION

We have now discovered that resistance of plants, particularly wheat and barley, to *Fusarium* head blight (FHB) and other *Fusarium*-related diseases may be induced or enhanced by genetic transformation with a recombinant nucleic acid (DNA) construct comprising a nucleic acid sequence encoding the wheat ethylene-responsive transcription factor TaERF7-1 operatively linked to a promoter effective for expression in the plant. Plants transformed with the construct exhibit increased resistance to FHB and other *Fusarium*-related diseases in comparison to a non-transformed control plant.

The transgenic plants may be produced from any plant, tissue or cell which is capable of regeneration, by transformation with the construct. Transformed plants, plant tissue or plant cells comprising the construct are selected, and the transgenic plant is generated therefrom.

In accordance with this discovery, it is an object of this invention to provide transgenic plants with improved resistance to FHB, and a method for their production.

Another object of this invention is to provide transgenic wheat and barley which exhibit increased resistance to FHB in comparison to a non-transformed control wheat and barley plants.

A further object of this invention is to provide nucleic acid constructs which may be used to transform plants, which transformed plants exhibit improved resistance to FHB.

Other objects and advantages of this invention will become readily apparent from the ensuing description.

BRIEF DESCRIPTION OF THE DRAWINGS

FIG. 1 shows the predicted amino acid sequence (SEQ ID NO: 1) of the wheat ethylene-responsive transcription factor TaERF7-1.

FIG. 2 shows the nucleotide sequence (SEQ ID NO: 2) as cloned into expression cassette as described in the Example. The underlined sequence (nucleotides 23-1165) is the cDNA sequence of the gene encoding wheat ethylene-responsive transcription factor TaERF7-1.

BRIEF DESCRIPTION OF THE SEQUENCES

The invention can be more fully understood from the following detailed description and the accompanying sequence descriptions, which form a part of this application.

```
                                               SEQ. ID. NO: 1
MCGGAILAGF IPPSAAAAAA KAAAAKKKQQ QRSVTADSLW

PGLRKKAAEE EDFEADFRDF ERDSSDDDAV VEEVPPPPAS

AGFAFAAAAE VAPPAPARLD AVQHDGPAAK QVKRVRKNQY

RGIRQRPWGK WAAEIRDPSK GVRVWLGTYD TAEEAARAYD
```

-continued

```
AEARKIRGKK AKVNFPEDAP TVQKSTLKPT AAKSAKLAPP

PKACEDEPFN HLSRGDNDLF AMFAFNDKKV PAKPAESVDS

LLPVKPLVPT ETFGMNMLSD QSSNSFGSTD FGWDDEVMTP

DYTSVFVPNA AAMPAYGEPA YLQGGAPKRM RNNFGVAVLP

QGNVAQDIPA FDHEMKYSLP YVESSSDGSM DSLLLNGAMQ

DGASSGDLWS LDELFMAAGG Y is predicted amino acid sequence for TaERF7-1.

SEQ. ID. NO: 2
ggatccttga tccggcctcg cgatgtgcgg cggagccatc ctcgcgggct tcatcccgcc gtcggcggcc gccgcggcgg ccaaggcggc ggcagccaag aagaagcagc agcagcgcag cgtgacggcc gactcgctgt ggccgggcct gcggaaaaag gcggccgagg aggaggactt cgaggccgac ttccgcgact tcgagcggga ctccagcgac gacgacgccg tggtcgagga ggttccaccg ccgccggcct cggcgggttt cgccttcgcc gccgcggccg aggtcgcgcc cccggcccct gcccgcctag atgctgttca acatgatgga cctgctgcca aacaagtaaa gcgcgttcgg aagaatcagt acagaggcat ccgccagcgt ccctggggga aatgggcagc tgaaatccgt gaccctagca agggtgtccg ggtttggctc gggacatacg acactgctga ggaggcagca agggcatatg atgctgaagc ccgcaagatt cgtggcaaga aggccaaggt caattttcct gaggatgctc caactgttca gaagtctact ctgaagccaa ctgccgctaa atcagcaaag ctggctccac ctccgaaggc ctgcgaggat gagcctttca atcatctgag cagaggagac aatgatttgt tcgcgatgtt cgccttcaat gacaagaaag ttcctgcgaa gccagctgaa agtgtggatt cccttcttcc ggtgaaacct cttgtgccca ctgagacatt cgggatgaac atgctctctg accagagtag caactcattt ggctctactg actttgggtg ggacgatgag gtcatgaccc cggactacac gtccgtcttc gtcccgaatg ctgctgccat gccggcatac ggcgagcccg cttacctgca aggtggagct ccaaagagaa tgaggaacaa ctttggcgtg gccgtgctgc ctcagggaaa tgttgcacaa gacatccctg cttttgacca tgagatgaag tactcgttgc cttatgttga gagcagctcg gacggatcaa tggacagcct tctgctgaat ggtgcgatgc aggacggggc aagcagtggg gatctctgga gcctcgatga gctcttcatg gcggctggtg gttactgagg gttcttgtct gtgtggatcc
``` is cDNA sequence for TaERF7-1.

DEFINITIONS

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage, cosmid, artificial chromosome (bacterial or yeast), or nucleic acid sequence which is able to replicate in a host cell, characterized by one or a small number of restriction endonuclease recognition sites at which the sequence may be cut in a predetermined fashion, and which may contain an optional marker suitable for use in the identification of transformed cells, e.g., tetracycline resistance or ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eukaryotic mRNA. A polyadenylation signal and transcription termination sequence will usually be located 3' to the coding sequence.

DNA Construct or Recombinant DNA Construct. Artificially constructed (i.e., non-naturally occurring) DNA molecules useful for introducing DNA into host cells, including chimeric genes, expression cassettes, and vectors.

DNA Sequence. A linear series of nucleotides connected one to the other by phosphodiester bonds between the 3' and 5' carbons of adjacent pentoses.

Expression. The process undergone by a structural gene to produce a polypeptide. Expression requires transcription of DNA, post-transcriptional modification of the initial RNA transcript, and translation of RNA.

Expression Cassette. A chimeric nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed, operably linked to a promoter. Typically, an expression cassette is part of an expression vector.

Expression Control Sequence. Expression control sequences are DNA sequences involved in any way in the control of transcription or translation and must include a promoter. Suitable expression control sequences and methods of making and using them are well known in the art.

Expression Vector. A nucleic acid which comprises an expression cassette and which is capable of replicating in a selected host cell or organism. An expression vector may be a plasmid, virus, retrovirus, bacteriophage, cosmid, artificial chromosome (bacterial or yeast), or nucleic acid sequence which is able to replicate in a host cell, characterized by a restriction endonuclease recognition site at which the sequence may be cut in a predetermined fashion for the insertion of a heterologous DNA sequence. An expression vector may include the promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Operably Linked, Encodes or Associated. Operably linked, operably encodes or operably associated each refer to the functional linkage between a promoter and nucleic acid sequence, wherein the promoter initiates transcription of RNA corresponding to the DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Phage or Bacteriophage. Bacterial virus many of which include DNA sequences encapsidated in a protein envelope or coat ("capsid"). In a unicellular organism a phage may be introduced by a process called transfection.

Plant. Plant refers to a unicellular organism or a multicellular differentiated organism capable of photosynthesis, including algae, angiosperms (monocots and dicots), gymnosperms (ginko, cycads, gnetophytes, and conifers), bryophytes, ferns and fern allies. Plant parts are parts of multicellular differentiated plants and include seeds, pollen, embryos, flowers, fruits, shoots, leaves, roots, stems, explants, etc.

Plant Cell. Plant cell refers to the structural and physiological unit of multicellular plants. Thus, the term plant cell refers to any cell that is a plant or is part of, or derived from, a plant. Some examples of cells encompassed by the present invention include differentiated cells that are part of a living plant, differentiated cells in culture, undifferentiated cells in culture, and the cells of undifferentiated tissue such as callus or tumors.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant."

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, i.e., occurring naturally to direct the expression of a nucleic acid derived from a gene other than the desired nucleic acid. A promoter may be constitutive or inducible. A constitutive promoter is a promoter that is active under most environmental and developmental conditions. An inducible promoter is a promoter that is active under environmental or developmental regulation, e.g., upregulation in response to wounding of plant tissues. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Replicon. Any genetic element (e.g., plasmid, chromosome, virus) that functions as an autonomous unit of DNA replication in vivo, i.e., capable of replication under its own control.

Start Codon. Also called the initiation codon, is the first mRNA triplet to be translated during protein or peptide synthesis and immediately precedes the structural gene being translated. The start codon is usually AUG, but may sometimes also be GUG.

Stringent Hybridization Conditions. The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will differ in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent hybridization conditions comprise hybridization in 50% formamide, 1 M NaCl, 1% SDS at 37° C., and a wash in 0.1×SSC at 60 to 65° C. It is also understood that due to the advances in DNA PCR and sequencing approaches that issues of gene identity and homology may be determined by sequence based rather than hybridization approaches.

Structural Gene. A DNA sequence which encodes through its template or messenger RNA (mRNA) a sequence of amino acids characteristic of a specific polypeptide.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In prokaryotes and yeast, for example, the exogenous DNA may be maintained on an episomal element such as a plasmid. With respect to eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Transcription Factor. A polynucleotide or polypeptide that controls the expression of a gene or genes either directly by binding to one or more nucleotide sequences associated with a gene coding sequence or indirectly by affecting the level or activity of other polypeptides that do bind directly or indirectly to one or more nucleotide sequences associated with a gene coding sequence. A transcription factor includes any polypeptide that can activate or repress transcription of a single gene or a number of genes.

Transgenic plant. A plant comprising at least one heterologous nucleic acid sequence that was introduced into the plant, at some point in its lineage, by genetic engineering techniques. Typically, a transgenic plant is a plant that is transformed with an expression vector. It is understood that a transgenic plant encompasses a plant that is the progeny or descendant of a plant that is transformed with an expression vector and which progeny or descendant retains or comprises the expression vector. Thus, the term "transgenic plant" refers to plants which are the direct result of transformation with a heterologous nucleic acid or transgene, and the progeny and descendants of transformed plants which comprise the introduced heterologous nucleic acid or transgene.

Translation. The process of producing a polypeptide from mRNA.

DETAILED DESCRIPTION OF THE INVENTION

In the following description, the nomenclature used to define the proteins and peptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

Transformation of plants with a recombinant DNA construct comprising a nucleic acid sequence encoding the wheat ethylene-responsive transcription factor TaERF7-1 confers significantly increased resistance to FHB and other *Fusarium*-related diseases in comparison to a non-transformed control plant (lacking the DNA construct). The TaERF7-1 protein may be expressed in the plant by use of DNA constructs wherein the nucleic acid sequence encoding the TaERF7-1 is operatively linked to a promoter which is active (i.e., functional or effective for expression) in the plant of interest. In contrast with the normal, non-transformed plants, plants which are transformed with this construct will express (including over-expression as in wheat) and accumulate the TaERF7-1 protein therein. Moreover, the encoded TaERF7-1 proteins are expressed at a sufficient level that the transgenic plants exhibit increased resistance to FHB and other *Fusarium*-related diseases in comparison to a non-transformed control plant (parent).

The gene encoding the wheat ethylene-responsive transcription factor TaERF7-1 protein has been isolated, cloned and sequenced. The nucleic acid sequence of the translated region of the cDNA encoding the TaERF7-1 corresponds to nucleotides 23-1165 of SEQ ID NO: 2 and is shown in FIG. 2 (underlined). The sequence shown in FIG. 2 also includes untranslated 3' and 5' regions (not underlined) as cloned into expression cassette as described in the Example. Without being bound to theory, the 5' untranslated sequences are thought to aid in the stabilization of mRNAs and influence the rate of translation, while 3' untranslated regions affect message stability and efficiency of mRNA polyadenylation. The encoded TaERF7-1 protein, shown in FIG. 1, is 381 amino acids long and has a predicted amino acid sequence corresponding to SEQ ID NO: 1. As used herein, isolated nucleic acid sequences refer to sequences which have been substantially separated from other nucleic acids or cell components which are normally present in the cells of the plant, such that the TaERF7-1 encoding sequences are the only significant sequences in the sample that can be used to express or produce the recombinant TaERF7-1 in a host cell as described below. The term encompasses not only nucleic acid sequences which have been recovered from naturally occurring cells, but also recombinant or cloned nucleic acid sequences, and synthesized nucleic acid sequences. The nucleic acid sequences may be recovered from cells of wheat plants, for example, by constructing a genomic DNA or cDNA library and screening for the TaERF7-1 nucleic acid using the disclosed sequences as probes. However, in a preferred embodiment, the sequences are synthesized using techniques established in the art for automated DNA synthesis or amplification. As used herein, the nucleic acid sequences of the TaERF7-1 encompass either or both of the coding strand or its complement.

Because of the degeneracy of the genetic code, there exists a finite set of nucleotide sequences which can code for a given amino acid sequence. Consequently, nucleic acids may be identical in sequence to the sequence which is naturally occurring or they may include alternative codons which encode the same amino acid as that which is found in the naturally occurring sequence. Furthermore, nucleic acids may include codons which represent conservative substitutions of amino acids as are well known in the art. Further still, different species can preferentially use different codons to code for the same amino acid and significant differences in tRNAs can exist. Thus, translation of recombinant proteins can often be enhanced by optimizing codon usage to the preferred codons used by the expression species. It is understood that all such equivalent sequences are operable variants of the disclosed TaERF7-1 gene sequence, since all give rise to the same TaERF7-1 protein (i.e., the same amino acid sequence, SEQ ID NO: 1) during in vivo transcription and translation, and are hence encompassed herein. DNA sequences which contain significant sequence similarity to the coding regions of the nucleotide sequence of nucleotides 23-1165 of SEQ ID NO: 2 are also encompassed by the invention. As defined herein, two DNA sequences contain significant sequence similarity when at least 85% (preferably at least 90% and most preferably 95%) of the nucleotides match over the defined length of the sequence. Sequences that are significantly similar can be identified in a Southern hybridization experiment under stringent hybridization conditions as is known in the art. See, for example, Sambrook et al., Molecular Cloning: A Laboratory Manual (2$^{nd}$ Ed.), Vol. 1-3, Cold Spring Harbor Laboratory, Cold Spring Harbor, N.Y., 1989, or DNA Cloning: A Practical Approach, Vol. I and II (Ed. D. N. Glover), IRL Press, Oxford, 1985.

The nucleic acid sequence encoding the TaERF7-1 protein in the construct will be operatively linked to a promoter which is active (i.e., functional or effective for expression) in the target plant. The promoter should provide a level of expression of the TaERF7-1 protein in the cells of the resultant transgenic plant such that this transgenic plant exhibits increased resistance to FHB and/or other *Fusarium*-related diseases in comparison to a non-transformed control plant (parent). A variety of promoters are effective for use herein, and include both constitutive and inducible promoters, although relatively strong constitutive promoters are preferred. Without being limited thereto, the preferred promoter for use herein is the constitutive maize Ubi1 promoter, described by Christensen et al. (1992. Plant Mol. Biol. 18:675-689) and Christensen and Quail (1996. Transgenic Res. 5:213-218), the contents of each of which are incorporated by reference herein). Barley Lem1 promoter (Skadsen et al. 2002. Plant Mol. Biol. 49:545-555) and barley Lem2 promoter (Anede et al. 2005. Planta. 221:170-183) may also be used, particularly in wheat and barley. By way of example, it is envisioned that other suitable promoters which may be used include: the rice actin Act-1 promoter (McElroy et al. 1990. Plant Cell. 2:163-171); the constitutive 35S RNA promoter of CaMV (Odell et al. 1985. Nature. 313:810-812); the full-length transcript promoter from Figwort Mosaic Virus (FMV) (Gowda et al. 1989. J. Cell Biochem. 13D:301); the coat protein promoter to TMV (Takamatsu et al. 1987. EMBO J. 6:307); the light-inducible promoter from the small subunit of ribulose bis-phosphate carboxylase (ssRUBISCO) (Coruzzi et al. 1984. EMBO J. 3:1671; and Broglie et al. 1984. Science. 224:838); mannopine synthase promoter (Velten et al. 1984. EMBO J. 3:2723); nopaline synthase (NOS) and octopine synthase (OCS) promoters (carried on tumor-inducing plasmids of *Agrobacterium tumefaciens*); and heat shock promoters, e.g., soybean hsp17.5-E or hsp17.3-B (Gurley et al. 1986. Mol. Cell. Biol. 6:559; and Severin et al. 1990. Plant Mol. Biol. 15:827). Other inducible promoters include those induced by chemical means, such as the yeast metallothionein promoter which is activated by copper ions (Mett et al. 1983. Proc. Natl. Acad. Sci., U.S.A. 90:4567); In2-1 and In2-2 regulator sequences which are activated by substituted benzenesulfonamides, e.g., herbicide safeners (Hershey et al. 1991. Plant Mol. Biol. 17:679); and the GRE regulatory sequences which are induced by glucocorticoids (Schena et al. 1991. Proc. Natl. Acad. Sci., U.S.A. 88:10421).

Various methods may be used to produce the DNA construct, expression cassette or vector comprising the TaERF7-1 nucleic acid sequence and promoter for transformation of the desired plant or its tissue or cells. The skilled artisan is well aware of the genetic elements that must be present on an expression construct/vector in order to successfully transform, select and propagate the expression construct in host cells. Techniques for manipulation of nucleic acids encoding promoter and the TaERF7-1 sequences such as subcloning nucleic acid sequences into expression vectors, labeling probes, DNA hybridization, and the like are described generally in Sambrook et al., [Molecular Cloning—A Laboratory Manual (2nd Ed.), Vol. 1-3, Cold Spring Harbor Laboratory, Cold Spring Harbor, N.Y., 1989] and Kriegler [Gene Transfer and Expression: A Laboratory Manual, 1990] or on public sites.

DNA constructs comprising the promoter operably linked to the TaERF7-1 DNA sequence can be inserted into a variety of vectors. Typically, the vector chosen is an expression vector that is useful in the transformation of plants and/or plant cells. Moreover, the expression constructs will typically comprise restriction endonuclease sites to facilitate vector construction and ensure that the promoter is upstream of and in-frame with silencing nucleic acid sequence. Exemplary restriction endonuclease recognition sites include, but are not limited to recognition site for the restriction endonucleases NotI, AatII, SacII, PmeI, HindIII, PstI, EcoRI, and BamHI.

The expression vector may be a plasmid, virus, cosmid, artificial chromosome, nucleic acid fragment, or the like. Such vectors can be constructed by the use of recombinant DNA techniques well known to those of skill in the art. The expression vector comprising the promoter sequence may then be transfected/transformed into the target host cells. Successfully transformed cells are then selected based on the presence of a suitable marker gene as disclosed below.

A variety of vectors may be used to create the expression constructs comprising TaERF7-1 nucleic acid sequence and promoter. Numerous recombinant vectors are known and available to those of skill in the art and are suitable for use herein for the stable transfection of plant cells or for the establishment of transgenic plants. Without being limited thereto, preferred vectors include those described by Christensen and Quail (1996. ibid, the contents of which are incorporated by reference herein), and particularly pAHC20 described therein. Other suitable vectors include those described, for example, by Weissbach and Weissbach (1989. Methods for Plant Molecular Biology, Academic Press), Gelvin et al. (1990. Plant Molecular Biology Manual: Genetic Engineering of plants, an Agricultural Perspective, A. Cashmore, Ed., Plenum: NY, 1983; pp 29-38), Coruzzi et al. (1983. The Journal of Biological Chemistry. 258:1399) and Dunsmuir et al. (1983. Journal of Molecular and Applied Genetics. 2:285). The choice of the vector is influenced by the method that will be used to transform host plants, and appropriate vectors are readily chosen by one of skill in the art.

Typically, the plant transformation vectors will include the promoter sequences operably linked to the TaERF7-1 nucleic acid sequence (DNA sequence) in the sense orientation, and a selectable marker. Such plant transformation vectors may also include a transcription initiation start site, a ribosome binding site, an RNA processing signal, a transcription termination site, and/or a polyadenylation signal, and it is also understood that the selectable marker, if present, may include an additional promoter and termination site. The plant transformation vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions. The expression constructs may further comprise an enhancer sequence. As is known in the art, enhancers are typically found 5' to the start of transcription, they can often be inserted in the forward or reverse orientation, either 5' or 3' to the TaERF7-1 sequence. Expression constructs prepared as disclosed herein may also include a sequence that acts as a signal to terminate transcription and allow for the poly-adenylation of the mRNA produced by the TaERF7-1 sequence operably linked to the promoter. Termination sequences are typically located in the 3' flanking sequence of the silencing sequences, which will typically comprise the proper signals for transcription termination and polyadenylation. Thus, in one embodiment, termination sequences are ligated into the expression vector 3' of the TaERF7-1 sequence to provide polyadenylation and termination of the mRNA. Terminator sequences and methods for their identification and isolation are known to those of skill in the art, see e.g., Albrechtsen et al. 1991. Nucleic Acids Res. April 25. 19(8):1845-1852, and WO/2006/013072. The transcription termination sequences comprising the expression constructs, may also be associated with known genes from the host organism. Yet other DNA sequences encoding additional functions may also be present in the vector, as is known in the art. For instance, in the case of *Agrobacterium* transformations, T-DNA sequences will also be included for subsequent transfer to plant chromosomes.

As noted above, plant transformation vectors typically include a selectable and/or screenable marker gene to allow for the ready identification of transformants. As is known in the art, marker genes are genes that impart a distinct phenotype to cells expressing the marker gene, such that transformed cells can be distinguished and/or selected from cells that do not have the marker (and thus have not incorporated the vector). Exemplary selectable marker genes include, but are not limited to, those encoding antibiotic resistance (e.g., resistance to hygromycin, kanamycin, bleomycin, G418, streptomycin or spectinomycin) and herbicide resistance genes (e.g., phosphinothricin acetyltransferase). In this embodiment, the marker genes encode a selectable marker which one can "select" for by chemical means, e.g., through the use of a selective agent (e.g., a herbicide, antibiotic, or the like). Alternatively, the marker genes may encode a screenable marker which is identified through observation or testing, e.g., by "screening". Exemplary screenable markers include e.g., green fluorescent protein.

A variety of selectable marker genes are known in the art and are suitable for use herein. Some exemplary selectable markers are disclosed in e.g., Potrykus et al. (1985. Mol. Gen. Genet. 199:183-188); Stalker et al. (1988. Science. 242:419-422); Thillet et al. (1988. J. Biol. Chem. 263: 12500-12508); Thompson et al. (1987. EMBO J. 6:2519-2523); Deblock et al. (1987. EMBO J. 6:2513-2518); U.S. Pat. No. 5,646,024; U.S. Pat. No. 5,561,236; U.S. Patent application Publication 20030097687; and Boutsalis and Powles (1995. Weed Research. 35:149-155).

Screenable markers suitable for use herein include, but are not limited to, a β-glucuronidase (GUS) or uidA gene, (see e.g., U.S. Pat. No. 5,268,463, U.S. Pat. No. 5,432,081 and U.S. Pat. No. 5,599,670); a β-gene (see e.g., Sutcliffe. 1978. Proc. Natl. Acad. Sci. USA. 75:3737-3741); β-galactosidase; and luciferase (lux) gene [see e.g., Ow et al. 1986. Science. 234:856-859; Sheen et al. 1995. Plant J. 8(5):777-784; and WO 97/41228]. Other suitable selectable or screenable marker genes also include genes which encode a "secretable marker" whose secretion can be detected as a means of identifying or selecting for transformed cells. Such secretable markers include, but are not limited to, secretable antigens that can be identified by antibody interaction (e.g., small, diffusible proteins detectable for example by ELISA); secretable enzymes which can be detected by their catalytic activity, such as small active enzymes detectable in extracellular solution (e.g., α-amylase, β-lactamase or phosphinothricin acetyltransferase); and proteins that are inserted or trapped in the cell wall (e.g., proteins that include a leader sequence such as that found in the expression unit of extensin or tobacco PR-S).

The DNA constructs containing the active promoter operably linked to the TaERF7-1 DNA sequence can be used to transform plants, plant tissue or plant cells and thereby generate transgenic plants which exhibit increased resistance to FHB and/or *Fusarium*-related diseases as described in the Example hereinbelow. Plants which may be transformed in accordance with this invention may be dicotyledonous or monocotyledonous species, and include, but are not limited to sorghum (*Sorghum vulgare*), alfalfa (*Medicago saliva*), sunflower (*Helianthus annus*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), wheat (*Triticum* spp), rice (*Oryza sativa*), barley (*Hordeum vulgare*), oats (*Avena sativa*), maize (*Zea mays*), rye (*Secale cereale*), onion (*Allium* spp), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), papaya (*Carica papaya*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), tomatoes; (*Solanum lycopersicum*), lettuce (e.g., *Lactuea sativa*), carrots (*Caucuis carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita*, e.g., Hubbard squash (*C. Hubbard*), Butternut squash (*C. moschtata*), Zucchini (*C. pepo*), Crookneck squash (*C. crookneck*), *C. argyrosperma, C. argyrosperma* ssp *sororia, C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*). Ornamental plants e.g., azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and *chrysanthemum*, and laboratory plants, e.g., *Arabidopsis*. Of these, maize, sorghum, and particularly wheat and barley, are preferred.

Transformation of plant, plant tissue or plant cell with the DNA construct comprising the nucleic acid sequence encoding a TaERF7-1 protein operatively linked to the promoter may be effected using a variety of known techniques. Techniques for the transformation and regeneration of monocotyledonous and dicotyledonous plant cells are well known in the art, see e.g., Weising et al. 1988. Ann. Rev. Genet. 22:421-477; U.S. Pat. No. 5,679,558; *Agrobacterium* Protocols Kevan M. A. Gartland ed. (1995) Humana Press Inc.; and Wang et al. 1998. Acta Hort. (ISHS). 461:401-408. A variety of techniques are suitable for use herein, and include, but are not limited to, electroporation, microinjection, microprojectile bombardment, also known as particle acceleration or biolistic bombardment, viral-mediated transformation, and *Agrobacterium*-mediated transformation. The choice of the preferred method for use herein will vary with the type of plant to be transformed, and may be readily determined by the skilled practitioner. Detailed descriptions of transformation/transfection methods are available and are disclosed, for example, as follows: direct uptake of foreign DNA constructs (see e.g., EP 295959); techniques of electroporation [see e.g., Fromm et al., 1986, Nature (London) 319:791]; high-velocity ballistic bombardment with metal particles coated with the nucleic acid constructs [see e.g., Kline et al. 1987. Nature (London). 327:70, and U.S. Pat. No. 4,945,050]; methods to transform foreign genes into commercially important crops, such as rapeseed [see De Block et al. 1989. Plant Physiol. 91:694-701], sunflower [Everett et al. 1987. Bio/Technology. 5:1201], soybean [Hinchee et al. 1988. Bio/Technology. 6:915; Finer and McMullen. 1991. In Vitro Cell Dev. Biol. 27P:175-182; and Olholft et al. 2003. Planta. 216:723-735], rice [Hiei et al. 1994. Plant J. 6:271-282], corn [Gordon-Kamm et al. 1990. Plant Cell. 2:603-618; Fromm et al. 1990. Biotechnology. 8:833-839], and Hevea (Yeang et al. In, Engineering Crop Plants for Industrial End Uses. Shewry, P. R., Napier, J. A., David, P. J., Eds. Portland: London, 1998, pp 55-64). Other suitable, known methods are disclosed in e.g., U.S. Pat. Nos. 5,597,945; 5,589,615; 5,750,871; 5,268,526; 5,262,316; and 5,569,831. In a preferred embodiment the transformation is effected using particle bombardment.

After transformation of the plant, plant tissue or plant cell, those plant cells transformed with the selected vector such that the construct is integrated therein can be cultivated in a culture medium under conditions effective to grow the plant or its cell or tissue. Successful transformants may be differentiated and selected from non-transformed plants or cells using a phenotypic marker. As described above, these phenotypic markers include, but are not limited to, antibiotic resistance, herbicide resistance or visual observation.

Transformed plant cells which are derived by any of the above transformation techniques can be cultured to regenerate a whole plant which possesses the desired transformed genotype of increased expression of TaERF7-1, and the phenotype of increased resistance to FHB and/or other *Fusarium* related diseases in comparison to non-transformed control plants. Plant regeneration techniques are well known in the art. For example, plant regeneration from cultured protoplasts is described in Evans et al., Protoplasts Isolation and Culture, Handbook of Plant Cell Culture, pp. 124-176, MacMillan Publishing Company, New York, 1983; and Binding, Regeneration of Plants, Plant Protoplasts, pp. 21-73, CRC Press, Boca Raton, 1985, all of which are incorporated herein by reference. Regeneration can also be obtained from plant callus, explants, organs, or parts thereof. Such regeneration techniques are described generally in Klee et al. 1987. Ann. Rev. of Plant Phys. 38:467-486, the content of which is also incorporated by reference herein.

The skilled artisan will recognize that different independent transformation events will result in different levels and patterns of expression (Jones et al. 1985. EMBO J. 4:2411 2418; and De Almeida et al. 1989. Mol. Gen. Genetics. 218:78-86), and thus that multiple events may need to be screened in order to obtain lines displaying the desired expression level of the TaERF7-1 protein. Exemplary methods for screening transformation events may be accomplished e.g., by Southern analysis of DNA blots (Southern. 1975. J. Mol. Biol. 98:503), Northern analysis of mRNA expression [Kroczek. 1993. Chromatogr. Biomed. Appl. 618(1-2): 133-145] and/or Western analysis of protein expression. Expression of the TaERF7-1 protein DNA can also be detected by measurement of the specific RNA transcription product. This can be done, for example, by RNAse protection or Northern blot procedures, or by antibody analyses. In another exemplary embodiment, protein expression is quantitated and/or detected in different plant tissues using a reporter gene, e.g., GUS.

In any event, in the preferred embodiment, transformed plants are screened for the desired increase in resistance to FHB and/or other *Fusarium*-related diseases in comparison to a non-transformed or wild-type control plant. As described in the Examples hereinbelow, increased resistance to FHB and/or other *Fusarium*-related diseases may be demonstrated, for example, by a significant reduction in the number of plants infected with FHB or other *Fusarium* related disease, or a significant reduction in the severity of FHB or other *Fusarium* related disease in infected plants, all in transformed plants in comparison to an untreated control. The actual increase in resistance exhibited by the resultant transgenic plants will vary with the particular promoter used, as well as host plant and the variety thereof, soil conditions, and geography. As a practical matter, transgenic plants produced in accordance with this invention will exhibit an increase in resistance to FHB and/or other *Fusarium* related disease of at least about 15%, preferably about 20%, and most preferably about 25% or higher, all in comparison to a non-transformed control (measured at a confidence level of at least 80%, preferably measured at a confidence level of 95%). Resistance to FHB and other diseases may be measured using a variety of conventional techniques. In a preferred embodiment, resistance may be measured in a greenhouse or in a field bioassay using the techniques such as described by Engle et al. (2003. Evaluation of inoculation methods to determine resistance reactions of wheat to *Fusarium graminearum*. Plant Dis. 87:1530-1535), the contents of which are incorporated by reference herein.

One of skill in the art will recognize that, after the construct comprising the TaERF7-1 protein encoding sequence operatively linked to a promoter is stably incorporated in transgenic plants and confirmed to be operable, plant tissue or plant parts of the transgenic plants may be harvested, and/or the seed collected. The seed may serve as a source for growing additional plants with tissues or parts having the desired genotype of increased expression of TaERF7-1, and the phenotype of increased resistance to FHB and/or other *Fusarium* related diseases in comparison to non-transformed control plants. The construct may also be introduced into other plants by sexual crossing of the transformed plants. Any of a number of standard breeding techniques can be used, depending upon the species to be crossed.

The following example is intended only to further illustrate the invention and is not intended to limit the scope of the invention which is defined by the claims.

EXAMPLE 1

Obtaining Full-Length cDNAs

Full-length wheat for TaERF7-1 was synthesized by DNA2.0 (Menlo Park, Calif.) having the DNA sequence shown in FIG. 2.

Plasmid Construction

The constitutive maize Ubi1 promoter (Christensen and Quail, 1996, ibid) was used for expression of the chimeric gene Ubi:ERF). Control constructs were generated in which the Ubi promoter drives the expression of the GUS gene. The GUS marker provides indication of the correct expression of each transgene and also provides a transgenic plant that is identical to experimental plant in every way except for the TaERF7-1 coding sequence to serve as control for comparison in the FHB interactions. The full-length cDNAs were assembled into the pACH17 expression cassette in which the cDNA was expressed by the maize Ubi1 promoter. The transgene was configured so that the primary transcript will contain a spliceable Ubi1 intron. All the transgene constructs were independently co-transformed into the scab-susceptible wheat variety "Bobwhite" with pACH20 (Christensen and Quail. 1996. ibid) which encodes the selectable marker for glyphosate resistance.

Transformation of Wheat

The transformations were performed by particle bombardment. To generate transgenic plants, immature wheat embryos (c.v "Bobwhite") were isolated 10-14 days post-anthesis and cultured as described by Altpeter and Vasil (1996. Plant Cell Reports. 16:12-17) and modified by Anand and Zhou (2003. J. Exp. Bot. 54:1101-1111). Sixteen hours after transformation via particle bombardment, calli were placed on a selection medium (5 mg/liter glufosinate) for 10 days, shoot-production medium for 2 weeks and then transferred to an elongation and rooting medium for two weeks. Once roots formed, the plants were transferred to soil. Recovered plants were initially screened for the presence of the bar gene by applying a freshly prepared aqueous solution of 0.2% Liberty (AgEvo USA, Pikeville, N.C.) to the midlamina portion (~2.5 cm long) of the second or third youngest leaf. As a routine procedure, only the transgenic plants with herbicide resistance were further analyzed phenotypically and genetically. These $T_0$ plants were further tested for presence of the bar gene and the gene of interest via PCR and Southern blots analyses and expression of the transgenes were verified by RT-PCR.

Evaluation of FHB Interaction in Transgenic Plants

The interaction of the T1 transgenic plants with *Fusarium graminearum* was compared to that of the transgenic controls in which the promoter Ubi promoter is fused to GUS. Our FHB assays with transgenic plants were performed in containment greenhouses or growth chambers. The extent of fungal spreading was evaluated visually and recorded photographically.

EXAMPLE 2

The TaERF1 construct of Example used in Example 1 for the transformation of wheat was used to transform barley.

Plants of the two-rowed malting barley cultivar Conlon or the European cultivar Golden Promise were grown in a greenhouse at 21-26° C., 16/8 h (light/dark) photoperiod supplied by sodium halide lamps or in a growth chamber at 16-20° C., 16/8 h (light/dark) photoperiod supplied by a mixture of fluorescent and incandescent lights (150 W/m). Immature embryos (2-4 mm in length) were harvested and cultured using the methods of Manoharan and Dahleen [2002. Genetic transformation of the commercial barley (*Hordeum vulgare* L.) cultivar Conlon by particle bombardment of callus. Plant Cell Rep 21:76-80), the contents of which are incorporated by reference herein. Culture media containing elevated levels of copper and boron and a reduced level of iron relative to standard Murashige and Skoog (1962. A revised medium for rapid growth and bioassays with tobacco tissue culture. Plant Physiol 15:473-497) medium were supplemented with BAP (6-benzylaminopurine) and 2,4-D (2,4-dichlorophenoxyacetic acid) and prepared by a modified autoclaving procedure (Dahleen and Bregitzer. 2002, An improved media system for high regeneration rates from barley immature embryo-derived callus of commercial cultivars. Crop Sci 42:934-938). Calli produced after 10-14 days were placed on medium containing 0.2 M. mannitol and 0.2 M sorbitol, then transformed using a biolistic particle gun (PDS-1000/He, Bio-Rad, Hercules, Calif.). Bombarded calli were kept on the medium overnight and placed on callus induction medium (Dahleen and Bregitzer. 2002, ibid) containing 3 mg/L 2,4-D and 5 mq/L bialaphos for selection. Selection and regeneration of transgenic plants were done as described by Manoharan and Dahleen (2002, ibid).

It is understood that the foregoing detailed description is given merely by way of illustration and that modifications and variations may be made therein without departing from the spirit and scope of the invention.

We claim:

1. A method of producing a transgenic plant comprising:
    a) transforming a plant cell with a recombinant DNA construct comprising a nucleic acid sequence encoding the wheat ethylene-responsive transcription factor TaERF7-1 operatively linked to a heterologous promoter effective for expression in said plant cell to generate a transformed plant cell;
    b) growing the transformed plant cell to a transgenic plant, wherein said TaERF7-1 comprises the amino acid sequence of SEQ ID NO: 1; and wherein said transgenic plant is wheat or barley; and
    c) selecting said transgenic plant which exhibit increased resistance to *Fusarium* head blight in comparison to a non-transformed control plant.

2. The method of claim 1, wherein said plant is wheat.

3. The method of claim 1, wherein said nucleic acid sequence comprises nucleotides 23-1165 of SEQ ID NO: 2.

4. The method of claim 1 wherein said construct further comprises an identifiable phenotypic marker, and said method further comprises screening or selecting said transgenic plant or said transgenic plant cell for the presence of said marker therein.

5. A transgenic plant that comprises a recombinant DNA construct comprising a nucleic acid sequence encoding the wheat ethylene-responsive transcription factor TaERF7-1 operably linked to a heterologous promoter effective for expression in said transgenic plant, wherein said TaERF7-1 comprises amino acid sequence of SEQ ID NO: 1; wherein said plant is wheat or barley; wherein the cells of said transgenic plant produce TaERF7-1 protein; and wherein said TaERF7-1 expressing transgenic plant has increased resistance to *Fusarium* head blight in comparison to a non-transformed control plant.

6. The transgenic plant of claim 5, wherein said transgenic plant is wheat.

7. The transgenic plant of claim 5, wherein said nucleic acid sequence comprises nucleotides 23-1165 of SEQ ID NO: 2.

8. A seed of the transgenic plant of claim 5; wherein the seed comprises said recombinant DNA construct comprising said nucleic acid sequence encoding said wheat ethylene-responsive transcription factor TaERF7-1 operably linked to said heterologous promoter.

9. A plant part of the transgenic plant of claim 5, wherein said plant part is selected from the group consisting of leaves, stems, roots, flowers, tissues, epicotyls, meristems, hypocotyls, cotyledons, pollen, ovaries, cells and protoplasts; wherein the plant part comprises said recombinant DNA construct comprising said nucleic acid sequence encoding said wheat ethylene-responsive transcription factor TaERF7-1 operably linked to said heterologous promoter.

10. A progeny plant produced by sexual or asexual reproduction of the plant of claim 5, wherein the progeny plant comprises said recombinant DNA construct comprising said nucleic acid sequence encoding said wheat ethylene-responsive transcription factor TaERF7-1 operably linked to said heterologous promoter, and wherein said progeny plant is wheat or barley.

11. The progeny plant of claim 10 that exhibits increased resistance to *Fusarium* head blight in comparison to a non-transformed control plant.

12. A method of increasing resistance of a transgenic plant against *Fusarium* head blight compared to the resistance of a wild-type plant against *Fusarium* head blight, said method comprising:
    a) transforming a wild-type plant cell with an expression vector to generate a transgenic plant cell; wherein said expression vector comprises a heterologous promoter operably linked to a polynucleotide encoding TaERF7-1 having the amino acid sequence of SEQ ID NO: 1;
    b) growing the transformed plant cell to a transgenic plant; and
    c) selecting said transgenic plant which exhibits increased resistance to *Fusarium* head blight in comparison to a non-transformed control plant, wherein said transgenic plant is wheat or barley, and wherein said transgenic plant produces TaERF7-1.

13. The method of claim 12, wherein said polynucleotide encoding TaERF7-1 comprises nucleotides 23-1165 of SEQ ID NO: 2.

14. The method of claim 12, wherein said transgenic plant produces elevated levels of TaERF7-1 compared to the levels of TaERF7-1 produced by said wild-type plant.

15. A transgenic wheat or barley plant or part thereof produced by the method of claim 12 and having increasing resistance against *Fusarium* head blight compared to the resistance of a wild-type wheat or barley plant against *Fusarium* head blight, wherein said transgenic wheat or barley plant or part thereof produces TaERF7-1.

* * * * *